United States Patent [19]

Yamazaki et al.

[11] Patent Number: 4,789,398

[45] Date of Patent: Dec. 6, 1988

[54] FLOWER-THINNING AGENT FOR FRUIT TREES

[75] Inventors: Toshihiko Yamazaki; Shoji Murase, both of Ibaragi; Tatsurou Motohashi, Tokyo, all of Japan

[73] Assignees: The Director, Fruit Tree Research Station, Ministry of Agriculture, Forestry and Fisheries Government of Japan, Ibaragi; Ajinomoto Co., Inc., Tokyo, both of Japan

[21] Appl. No.: 843,679

[22] Filed: Mar. 25, 1986

[30] Foreign Application Priority Data

Apr. 2, 1985 [JP] Japan .................................. 60-68429

[51] Int. Cl.⁴ .............................................. A01N 31/00
[52] U.S. Cl. ..................................................... 71/122

[58] Field of Search ...................................... 71/122, 70

[56] References Cited

U.S. PATENT DOCUMENTS 4,613,359 9/1986 Yamazaki et al. .................... 71/122

FOREIGN PATENT DOCUMENTS 0089805 9/1983 European Pat. Off. .

Primary Examiner—Catherine L. Mills
Attorney, Agent, or Firm—Larson and Taylor

[57] ABSTRACT

A new flower-thinning agent is now provided, which is comprising cholesterol as the active component and advantageously exerts the flower-thinning effects superior to the known flower-thinning agents.

4 Claims, No Drawings

FLOWER-THINNING AGENT FOR FRUIT TREES

SUMMARY OF THE INVENTION

This invention relates to a new flower-thinning agent for use in the thinning treatment of flowers of fruit trees of various kinds. More particularly, this invention relates to a new flower-thinning agent which is applied to the flowers of cultivated fruit trees, for the purpose of partially removing or thinning the such flowers which are not required to undergo the fructification, while retaining on the tree such flowers which are required to fructify.

BACKGROUND OF THE INVENTION

In the cultivation of fruit trees of various kinds, it is essential to carry out preliminary work of picking off some of the flowers or fruit which are not required to fructify. This work of picking off the unrequired bodies of flowers or fruit is known as "thinning" of the flowers or fruit. Meanwhile, this thinning of the flowers or fruit usually requires a large amount of labor by workers. The thinning work must be done usually in the busy seasons of agriculture, and hence it is frequently difficult to carry out the thinning work at an appropriate time, so that the quality of the fruits cultivated and harvested is therefore sometimes lowered.

Heretofore, the methods for thinning the flower or fruit of fruit trees by chemical compounds have been extensively researched for almost all kinds of fruit trees such as apple tree, peach tree and others, and there has been proposed and developed a number of chemical thinning agents. The known chemical thinning agents may be classified according to their biological mechanisms of the action of these agents, and they may generally be classified into two groups, that is, a first group of such agents which act as a plant hormone and the second group of such agents which can exert phytotoxicity against the bodies or different organs of the flowers of fruit trees. While, such chemical thinning agents which have been extensively applied in practice for partial removal of the unrequired flowers or fruits are limited only to the formulation known under the name "Ethyclozate" for use in the thinning treatment of tangerine tree; the formulation known under the name "Sevin" for use in the thinning treatment of apple tree; and certain sulfur preparations for use in the thinning treatment of apple tree. The active components of the thinning agents known under the names "Ethyclozate" and "Sevin" belong to a class of plant hormone in nature, so that their flower-thinning effects can vary unfavorably depending on the biological conditions, of the trees treated and also on the weathering conditions, which is specifically observed with the plant hormone agents in general. On the other hand, the sulfur preparations practically employed as the chemical thinning agent are active in inhibiting the fertilization of flowers owing to its phytotoxicity to the stigma of the flower body, so that its flower-thinning activity is normally lower than those of the flower-thinning agents of plant hormone type. When the sulfur preparations are applied in an increased rate of application in an attempt to enhance its flower-thinning effects, the leaves and other portions of the fruit trees treated can often be damaged by the phytotoxicity of the sulfur preparations For these reasons, there exists a great demand for a new flower-thinning chemical agent which is free from the above-mentioned drawbacks of the known chemical flower-thinning agents. In an attempt to meet this demand, we previously investigated a number of chemical compounds which were different in nature from the active components of the known thinning agents, and we already found that 2-pyrrolidone-5-carboxylic acid and salts thereof such as the sodium salt; and salts of an N-acylaminodicarboxylic acid; as well as esters of sucrose with a higher fatty acid and plant sterols were each active in thinning the flowers of the cultivated fruit trees. Flower-thinning agent comprising the above-mentioned compounds as the active component are disclosed in the specifications of European Patent Publication No. 0089205 A2 (published on Sept. 21, 1983) and U.S. Ser. No. 473,354.

We have further investigated in an attempt to find out other chemical compounds which are effective in the thinning of flowers and fruit and we have now found that cholesterol is active as a flower-thinning agent.

DETAILED DESCRIPTION OF THE INVENTION

According to an aspect of this invention, therefore, there is provided a new flower-thinning agent comprising as the active component an effective amount of cholesterol, in association with a suitable liquid or solid carrier for the active component.

According to a further aspect of this invention, there is provided a method for thinning flowers of cultivated fruit trees, which comprises applying to the flowers and/or to the body of the fruit trees an effective amount of cholesterol.

This invention also includes use of cholesterol as a flower-thinning agent.

The flower-thinning agent according to this invention is applied to a fruit tree on the flowering time. The flower-thinning agent of this invention may be applied to a wide variety of fruit trees such as, for example, pear, peach, persimmon, apple, cherry and so on.

The flower-thinning agent according to this invention may be formulated into various form such as a solution, wettable powder, emulsion or spray, by mixing with any suitable solid or liquid carrier such as water. It is preferable that the thinning agent is applied in the form of an aqueous emulsion or dispersion of cholesterol as the active component. Such an aqueous emulsion or dispersion of cholesterol may be prepared using surface-active esters of sorbitol with a fatty acid, esters of polyhydric alcohol with a fatty acid, or lecithin as a dispersing agent.

The time of application of the flower-thinning agent of this invention may be chosen to be conducted either before or after the spontaneous or artificial pollination of the flowers, so that the flower-thinning effect obtained will reach a desired extent. Besides, the concentration of the cholesterol in the thinning agent as applied may also be chosen appropriately so that the flower-thinning effect obtained will reach a desired extent according to the nature of the fruit tree as treated.

The concentration of the cholesterol in the thinning agent may vary, in general, depending on the nature of the fruit tree treated and also on the environmental conditions when the agent is applied, but the concentration of cholesterol is usually in a range of 0.005 to 1.0% by weight, preferably, 0.005 to 0.02% by weight and especially 0.01 to 0.02% by weight.

The flower thinning agent according to this invention may be applied at a rate of 80 to 120 l, usually, 100 l per 10 ares of a place where the fruit trees to be treated are planted.

The flower-thinning agent according to this invention may optionally contain one or more of plant serols, such as for example, sitosterol, campesterol, stigmasterol and brassicasterol, in combination with the cholesterol.

The flower-thinning agent according to this invention has the following advantageous characteristics:

(1) The agent of this invention does not exhibit the flower-thinning effect against those flowers of which the fertilization has been finished, and thus it is possible to select the class of fruit trees from which the flowers are to be removed by the thinning treatment, if one choose the time when the agent is applied.

(2) The agent of this invention has no phytotoxicity to the plant to which it is applied.

(3) The agent of this invention may effectively be applied to a wide variety of fruit trees.

(4) The agent of this invention has no toxicity against humans and does not cause any environmental pollution.

(5) The agent of this invention is inexpensive.

The following Examples illustrate the invention.

EXAMPLE 1

An emulsion of 1% (by weight) of cholesterol in water was prepared by mixing together 1 part (by weight) of cholesterol, 15 parts of soya lecithin, 20 parts of ethyl acetate, 13 parts of stearic acid monoglyceride and 51 parts of water.

The emulsion as thus obtained was diluted with water to form an emulsion preparation containing the cholesterol at a desired, particular concentration.

EXAMPLE 2

An aqueous emulsion containing 2% (by weight) of a mixture of cholesterol and plant sterols comprising 50% (by weight) of β-sitosterol, 28% of campesterol, 15% of stigmasterol and 7% of brassicasterol (ratio by weight of cholesterol to the plant sterols=80/20) was prepared by mixing together 2 parts (by weight) of the mixture of cholesterol and plant sterols, 15 parts of soya lecithin, 10 parts of stearic acid monoglyceride, 20 parts of ethyl acetate and 53 parts of water. The resultant emulsion was diluted with water to form an emulsion preparation of a desired particular concentration of the sterols. (Hereinafter, a preparation containing the mixture of cholesterol and the plant sterols is referred to as "mixed agent" or "cholesterol/sterol agent").

The following Examples illustrate the flower-thinning effects of the thinning agent of this invention.

EXAMPLE 3

Flower Thinning of Japanese Pear Tree

The flower-thinning agents of this invention as prepared according to the foregoing Examples 1 to 2 and containing the active component compounds at a concentration of 0.005 to 0.03% (by weight) were sprayed onto the flowers of Japanese pear trees (Variety: Housui).

Said thinning agents as sprayed were applied at a rate of 100l per 10 ares.

The thinning effects of the agent applied were estimated by counting the number of all the individual flower bodies initially tested (termed as "number of flowers tested"), the number of flower clusters initially tested, the total number of fructified, individual flower bodies in the flower clusters (termed as "number of fructified flowers") and the number of the flower clusters of which any individual flower bodies had been fructified (termed as "number of fructified flower clasters) and evaluating "percentage of fruit set" (which means percentages of the total number of the fructified, individual flower bodies in the flower clusters, as calculated on the basis of the total number of the fructified and unfructified individual flower bodies in the flower clusters which were remaining on the tree even after the thinning treatment) and "percentage of bearing clusters" (which means percentages of the number of the flower clusters of which any individual flower body had been fructified, as calculated on the basis of the total number of the flower clusters which were remaining on the tree even after the thinning treatment).

Tables 1 to 5 given below show the influences on the flower thinning effects (percentage of fruit set and percentage of bearing cluster) of (a) the concentration of the active component in the emulsion applied, (b) the time of spraying the emulsion and (c) spraying of the emulsion on a flower-bud.

The thinning effects were estimated after 30 days after the spraying of the emulsion.

TABLE 1

| | Influence of the Concentration of Cholesterol on the flower thinning effect. | | | | | | |
|---|---|---|---|---|---|---|---|
| Active component | Concentration of the active component (%) | Number of flowers tested | Number of flower clusters tested | Number of fructified flowers | Number of fructified flower clusters | Percentage of fruit set (%) | Percentage of bearing clusters (%) |
| Cholesterol | 0.005 | 298 | 52 | 159 | 50 | 53.3* | 96.0 |
| | 0.01 | 297 | 54 | 138 | 49 | 46.5** | 90.6** |
| | 0.02 | 386 | 59 | 60 | 38 | 15.6** | 64.4** |
| Control | | 368 | 58 | 297 | 58 | 80.7 | 100.0 |
| (Untreated) | | 407 | 54 | 328 | 54 | 80.6 | 100.0 |

*Significance at 5% level.
**Significance at 1% level.

TABLE 2

| | Influence of the Concentration of the Mixed Agent (cholesterol/plant sterols: at ratio of 80/20 by weight) on the flower thinning effect when applied prior to the pollination | | | | | | |
|---|---|---|---|---|---|---|---|
| Active component | Concentration of the active component (%) | Number of flowers tested | Number of flower clusters tested | Number of fructified flowers | Number of fructified flower clusters | Percentage of fruit set (%) | Percentage of bearing clusters (%) |
| Mixed | 0.005 | 173 | 27 | 61 | 21 | 35/3$^a$ | 77.8 |

TABLE 2-continued

Influence of the Concentration of the Mixed Agent (cholesterol/plant sterols: at ratio of 80/20 by weight) on the flower thinning effect when applied prior to the pollination

| Active component | Concentration of the active component (%) | Number of flowers tested | Number of flower clusters tested | Number of fructified flowers | Number of fructified flower clusters | Percentage of fruit set (%) | Percentage of bearing clusters (%) |
|---|---|---|---|---|---|---|---|
| Agent | 0.01 | 199 | 28 | 73 | 23 | 36.7$^a$ | 82.1 |
|  | 0.02 | 160 | 29 | 68 | 26 | 42.5$^a$ | 89.7 |
|  | 0.03 | 191 | 27 | 73 | 24 | 38.2$^a$ | 88.9 |
| Control (Untreated) |  | 314 | 62 | 259 | 61 | 82.5$^b$ | 98.4 |

$^{a,b}$Statistical treatment is based on Mean separation within column by Duncan's multiple range test, 5% level.

TABLE 3

Influence of Time of Spraying the Mixed Agent (cholesterol/plant sterols: at ratio of 80/20 by weight) on the flower thinning effect (Spray after Pollination).

| Time of spraying the mixed agent (0.015% active component concentration) | Number of flowers tested | Number of flower clusters tested | Number of fructified flowers | Number of fructified flower clusters | Percentage of fruit set (%) | percentage of bearing clusters (%) |
|---|---|---|---|---|---|---|
| Immediately after pollination | 151 | 34 | 55 | 30 | 36.4$^a$ | 88.2 |
| 12 hours after pollination | 137 | 36 | 113 | 36 | 82.5$^b$ | 100.0 |
| 1 day after pollination | 188 | 37 | 122 | 36 | 64.9$^b$ | 97.3 |
| 2 days after pollination | 179 | 38 | 124 | 37 | 69.3$^b$ | 97.4 |
| 3 days after pollination | 125 | 24 | 86 | 24 | 68.8$^b$ | 100.0 |
| Control (untreated) | 314 | 62 | 259 | 61 | 82.5$^b$ | 98.4 |

TABLE 4

Influence the Time of Spraying the Mixed Agent (cholesterol/plant sterols: at ratio of 80/20 by weight) on the flower thinning effect (Spray before Pollination).

| Time of spraying the mixed agent (0.015% active component concentration) | Number of flowers tested | Number of flower clusters tested | Number of fructified flowers | Number of fructified flower clusters | Percentage of fruit set (%) | Percentage of bearing clusters (%) |
|---|---|---|---|---|---|---|
| 12 hours before pollination | 151 | 23 | 54 | 19 | 35.8$^a$ | 82.6 |
| 1 day before pollination | 198 | 29 | 65 | 22 | 32.8$^a$ | 75.9 |
| 2 days before pollination | 172 | 28 | 137 | 27 | 79.7$^b$ | 96.4 |
| Control (Untreated) | 314 | 62 | 259 | 61 | 82.5$^b$ | 98.4 |

TABLE 5

Influence of Spraying the Mixed Agent (cholesterol/plant sterols: at ratio of 80/20 by weight) onto flower-bud, on the flower thinning effect.

| Time of spray of the agent | Number of flowers tested | Number of flower clusters tested | Number of fructified flowers | Number of fructified flower clusters | Percentage of fruit set (%) | Percentage of bearing clusters (%) |
|---|---|---|---|---|---|---|
| 1 day before | 166 | 28 | 160 | 28 | 96.4$^a$ | 100.0 |
| Control (Untreated) | 314 | 62 | 259 | 61 | 82.5$^b$ | 98.4 |

EXAMPLE 4

Flower Thinning of Peach Tree

Using the emulsion preparation as prepared according to Example 2, there was evaluated the flower thinning effect on peach tree (variety: Nishiki) of the flower-thinning agent according to this invention.

In this Example, the thinning effects of the agent applied were estimated by counting the number of all the individual flower bodies initially tested (namely, "number of flowers tested" as defined before), the number of newly shot branches initially tested, the total number of fructified, individual flower bodies on the newly shot brances (termed as "number of fructified flowers") and the number of the newly shot brances of which any individual flower bodies had been fructified (termed as "number of fructified, newly shot brances") and evaluating "percentage of fruit set" (which means percentages of the total number of the fructified, individual flower bodies on the newly shot branches, as calculated on the basis of the total number of the fructified and unfructified individual flower bodies on the newly shot branches and "percentage of bearing, newly shot branches" (which means percentages of the number of the newly shot branches of which any individual flower body had been fructified, as calculated on the basis of the total number of the newly shot branches).

The thinning effects were estimated 30 days after the spraying of the emulsion.

Test results obtained are shown in Tables 6 and 7. Table 6 shows influence of the concentration of the mixed agent (ratio by weight of cholesterol/plant sterols: 80/20) on the thinning effect. Table 7 shows the thinning effect of the mixed agent which was applied after the pollination.

TABLE 6

Influence of the concentration of the mixed agent on the flower thinning effect.

| Concentration of the active component (%) | Number of flowers tested | Number of newly shot branches tested | Number of fructified flowers | Number of fructified newly shot branches | Percentage of fruit set (%) | Percentage of bearing newly shot branches (%) |
|---|---|---|---|---|---|---|
| 0.005 | 301 | 38 | 116 | 38 | 38.5$^a$ | 100.0 |
| 0.01 | 243 | 35 | 125 | 33 | 51.4$^{ab}$ | 94.3 |
| 0.02 | 275 | 35 | 116 | 33 | 42.4$^a$ | 94.3 |
| Control (Untreated) | 258 | 33 | 169 | 32 | 65.5$^b$ | 97.0 |

TABLE 7

Influence of the mixed agent when applied after the pollination on the flower thinning effect.

| Time of the spray of the mixed agent (0.015% active component concentration) | Number of flowers tested | Number of newly shot branches tested | Number of fructified flowers | Number of fructified newly shot branches | Percentage of fruit set (%) | Percentage of bearing newly shot branches (%) |
|---|---|---|---|---|---|---|
| 1 day after pollination | 105 | 24 | 58 | 22 | 55.2$^a$ | 91.7 |
| 2 days after pollination | 72 | 12 | 56 | 12 | 77.8$^b$ | 100.0 |
| 3 days after pollination | 73 | 9 | 52 | 9 | 71.2$^b$ | 100.0 |
| Control (Untreated) | 258 | 33 | 169 | 32 | 65.5$^b$ | 97.0 |

EXAMPLE 5

Flower Thinning of Apple Trees

The emulsion preparations as prepared according to the Example 1 above and containing cholesterol as the active agent at a concentration of 0.01 to 0.04% (by weight) were sprayed onto the flowers of apple trees (Variety: Orin).

The tests of this Example were carried out sucessively for 3 days at the beginning of May.

In this Example, the thinning effects of the agent applied were estimated by evaluating "percentage of fruit set in respect to lateral flowers", which means percentage of the total number of fructified lateral flower bodies in the flower clusters tested, as calculated on the basis of the total number of fructified and unfructified lateral flower bodies in the flower clusters tested which were remaining on the trees even after the thinning treatment, and also by evaluating "percentage of fruit set in respect to central flowers", which means percentage of the total number of fructified central flower bodies in the flower clusters tested, as calculated on the basis of the total number of the fructified and unfructified central flower bodies in the flower clusters tested which were remaining on the trees after the thinning treatment.

The thinning effects were estimated 30 days after the spray of the thinning agent.

The test results are shown in the Table 8.

TABLE 8

| Time of Spray of Flower Thinning Agent | Concentration of Active Component (%) | Percentage of Fruit Set (%) | |
|---|---|---|---|
| | | Lateral Flower of Flower Cluster | Central Flower of Flower Cluster |
| 2 days after full bloom of central flower. (Manual pollination was effected 2 hours before spraying). | 0.04 | 43.2 | 78.2 |
| | 0.02 | 67.5 | 87.5 |
| | 0.01 | 76.9 | 96.8 |
| 3 days after full bloom of central flower. (Manual pollination was effected 1 day before spraying). | 0.04 | 77.5 | 88.2 |
| | 0.02 | 42.5 | 88.5 |
| | 0.01 | 65.0 | 91.2 |
| 4 days after full bloom of central flower. (Manual pollination was effected 2 days before spraying). | 0.04 | 87.5 | 92.9 |
| | 0.02 | 76.3 | 95.8 |
| | 0.01 | 87.5 | 91.0 |
| Control (Untreated) | | 80.0 | 98.4 |

From the Table 8, it is evident that remarkable thinning effects can be obtained when the thinning agent is sprayed 2 days after the full bloom of central flowers. Particularly, the percentages of fruit set in respect to lateral flowers are lowered when the active component is applied at concentrations of 0.02% and 0.04%.

The percentages of fruit set in respect to the lateral flowers are lowered also when the thinning agent is applied 3 days after the full bloom of the central flowers.

However, no thinning effect can be obtained when the thinning agent is applied 4 days after the full bloom of the central flowers and 2 days after the pollination.

We claim:

1. A method for thinning flowers of cultivated fruit trees, which comprises applying to the flowers and/or to the body of the fruit trees an effective amount of a flower-thinning composition comprising cholesterol.

2. The method of claim 1 in which cholesterol is applied as an aqueous dispersion containing the cholesterol at a concentration of 0.005% to 0.02% by weight of cholesterol.

3. The method of claim 1 in which cholesterol is applied to the flowers prior to the pollination of the flowers.

4. The method of claim 1 in which cholesterol is applied to the flowers after the pollination of the flowers.

* * * * *